United States Patent [19]

Walker

[11] 4,078,071

[45] Mar. 7, 1978

[54] DERIVATIVES OF SUBSTITUTED N-ALKYL IMIDAZOLES

[75] Inventor: Keith A. M. Walker, Palo Alto, Calif.

[73] Assignee: Syntex (U.S.A.) Inc., Palo Alto, Calif.

[21] Appl. No.: 758,094

[22] Filed: Jan. 10, 1977

Related U.S. Application Data

[63] Continuation-in-part of Ser. No. 665,023, Mar. 8, 1976, abandoned, which is a continuation-in-part of Ser. No. 599,618, Jul. 28, 1975, abandoned.

[51] Int. Cl.² .................. A61K 31/415; C07D 233/60
[52] U.S. Cl. ............................... 424/273 R; 542/413; 548/341
[58] Field of Search ............... 260/309, 240 D, 240 J; 424/273

[56] References Cited

U.S. PATENT DOCUMENTS

| | | | |
|---|---|---|---|
| 3,658,813 | 4/1972 | Godefroi et al. | 260/309 |
| 3,682,951 | 8/1972 | Kreider | 260/309 |
| 3,717,655 | 2/1973 | Godefroi et al. | 260/309 |
| 3,796,704 | 3/1974 | Metzger et al. | 260/309 |

OTHER PUBLICATIONS

Conant et al., The Chemistry of Organic Compounds, Revised Edition, p. 264, N. Y., MacMillan, 1939.

*Primary Examiner*—Natalie Trousof
*Attorney, Agent, or Firm*—Alan M. Krubiner

[57] ABSTRACT

Compounds of the formula

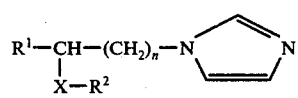
(I)

wherein $R^1$ and $R^2$ are each independently phenyl, phenyl straight chain lower alkyl or phenyl straight chain lower alkenyl or one of the above substituted in the phenyl ring with one or more substituents independently selected from the group consisting of lower alkyl of from one to four carbon atoms, halo and trifluoromethyl; X is oxygen or sulfur; $n$ is an integer of from 1 to 8 with the proviso that $n$ is not 1 when $R^1$ is phenyl or substituted phenyl; and the antimicrobial acid addition salts thereof are useful as antifungal, antibacterial and antiprotozoal agents.

35 Claims, No Drawings

DERIVATIVES OF SUBSTITUTED N-ALKYL IMIDAZOLES

RELATED APPLICATIONS

This case is a continuation-in-part of U.S. application Ser. No. 665,023, filed Mar. 8, 1976, abandoned, which in turn is a continuation-in-part of U.S. application Ser. No. 599,618, filed July 28, 1975, abandoned.

DETAILED DESCRIPTION OF THE INVENTION

The present invention relates to novel chemical compounds which are derivatives of substituted N-alkyl imidazoles. More particularly, the compounds of the present invention are represented by the formula

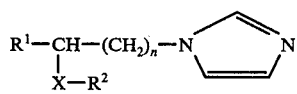
(I)

wherein $R^1$ and $R^2$ are each independently phenyl, phenyl straight chain lower alkyl, or phenyl straight chain lower alkenyl; or one of the above substituted in the phenyl ring with one or more substituents independently selected from the group consisting of lower alkyl of from one to four carbon atoms, halo and trifluoromethyl; X is oxygen or sulfur; n is an integer of from 1 to 8 with the proviso that n is not 1 when $R^1$ is phenyl or substituted phenyl; and the antimicrobial acid addition salts thereof.

In a second aspect the present invention is concerned with a method of combatting fungi, bacteria and protozoa by administering a compound of the present invention or a composition containing same.

As used in the specification and the appended claims, unless specified to the contrary, the following terms have the meaning inidicated. The term "lower alkyl" refers to a straight or branched chain monovalent substituent consisting solely of carbon and hydrogen, containing no unsaturation, and having from one to eight carbon atoms. Examples of lower alkyl groups are methyl, ethyl, n-propyl, i-propyl, n-butyl, t-butyl, pentyl, n-hexyl, and n-octyl. The term "lower alkenyl" refers to a straight or branched chain monovalent substituent consisting solely of carbon or hydrogen containing mono-olefinic unsaturation, and having from 2 to 8 carbon atoms. Examples of lower alkenyl groups are ethenyl, prop-1-enyl, prop-2-enyl, but-1-enyl, but-2-enyl, pent-1-enyl, pent-3-enyl, hex-1-enyl, hex-3-enyl, hex-5-enyl, hept-1-enyl, hept-4-enyl, hept-6-enyl, oct-1-enyl, oct-5-enyl, and oct-7-enyl. The term "styryl" refers to α-styryl. The term "halo" refers to fluoro, chloro and bromo. "Antimicrobial acid addition salts" of the subject bases refers to those salts which retain the antimicrobial properties of the free bases and which are neither biologically or otherwise undesirable, formed with, for example, inorganic acids such as hydrochloric acid, hydrobromic acid, sulfuric acid, nitric acid or phosphoric acid; or inorganic acids such as acetic acid, propionic acid, glycolic acid, lactic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. It is also understood, for purposes of this invention, that the phenyl rings of $R^1$ and $R^2$ cannot be substituted with three or more adjacent branched alkyl and/or trifluoromethyl groups.

All compounds of formula (I) possess at least one chiral center, i.e., the carbon atom to which are attached the $R^1$, X, $(CH_2)_n$ and H moieties. Accordingly, the compounds of the present invention may be prepared in either optically active form, or as a racemic mixture. Unless otherwise specified, the compounds described herein are all in the racemic form. However, the scope of the subject invention herein is not to be considered limited to the racemic form, but to encompass the individual optical isomers of the subject compounds. Additionally, those compounds possessing a substituted or unsubstituted phenyl straight chain lower alkenyl group can have geometric (cis and trans) isomers about the double bond. Both isomers as well as mixtures thereof are intended to be included within the scope of the present invention.

If desired, racemic intermediates or final products prepared herein may be resolved into their optical antipodes by conventional resolution means known per se, for example, by the separation (e.g., fractional crystallization) of the diastereomeric salts formed by reaction of, e.g., racemic compounds of formula (I) with an optically active acid, or by the separation of the diastereomeric salts or esters formed by reaction of racemic compounds of formula (II), infra, with an optically active acid. Exemplary of such optically active acids are optically active forms of camphor-10-sulfonic acid, α-bromo-camphor-π-sulfonic acid, camphoric acid, menthoxy-acetic acid, tartaric acid, malic acid, diacetyltartaric acid, pyrrolidone-5-carboxylic acid, and the like. The separated pure diastereomeric salts or esters may then be cleaved by standard means to afford the respective optical isomers of the compounds of formula (I) or (II).

The subject compounds of formula (I) exhibit antifungal, anti-bacterial and anti-protozoal activity. For example, compounds of the present invention exhibit anti-fungal activity against human and animal pathogens such as

*Microsporum audouini,*
*Microsporum gypseum,*
*Microsporum gypseum - canis,*
*Epidermophyton floccosum,*
*Trichophyton mentagrophytes,*
*Trichophyton rubrum*
*Trichophyton tonsurans*
*Candida albicans,* and
*Cryptococcus neoformans.*

The compounds of the present invention also exhibit anti-fungal activity against the following fungi primarily of agricultural significance

*Aspergillus flavus,*
*Cladosporium herbarum,*
*Fusarium graminearum,*
*Penicillium notatum,* and
*Aspergillus niger*
*Penicillium oxalicum,*
*Penicillium spinulosum,*
*Pithomyces chartarum.*

In addition, the compounds of the present invention exhibit anti-bacterial activity against human and animal pathogens, such as

*Staphylococcus aureus,*
*Streptococcus faecalis,*
*Corynebacterium acnes,*
*Erysipelothrix insidiosa,*

*Escherichia coli,*
*Proteus vulgaris,*
Salmonella choleraesuis,
*Pasteurella multocida,* and
*Pseudomonas aeruginosa.*

Moreover, the compounds of the present invention exhibit anti-protozoal activity against protozoa such as Trichomonas vaginalis.

In general, the subject compounds of the instant invention exhibit a low level of toxicity. Moreover, these compounds demonstrate good solubility in the stratum corneum. Since dermatophyte (i.e., parasitic fungal) infections are usually localized in the dead tissue of the stratum corneum, solubility of anti-fungal agents in this tissue significantly enhances their effectiveness.

In view of the aforementioned activities, the subject compounds are found to be useful antimicrobials, having not only pharmaceutical but also agricultural and industrial application.

Accordingly, a further aspect of the present invention relates to compositions for pharmaceutical, agricultural, and industrial use, which compositions comprise the subject compounds of formula (I) in combination with a suitable carrier. A still further aspect of the present invention relates to methods of inhibiting the growth of fungi, bacteria and protozoa by applying to a host object containing, or subject to attack by, fungi, bacteria or protozoa, an effective amount of a compound of the present invention or a suitable composition containing same.

In pharmaceutical applications, compositions may be solid, semi-solid or liquid in form such as tablets, capsules, powders, suppositories, liquid solutions, suspensions, creams, lotions, ointments and the like. Pharmaceutically acceptable non-toxic carriers, or excipients normally employed for solid formulations include tricalcium phosphate, calcium carbonate, kaolin, bentonite, talcum, gelatin, lactose, starch and the like; for semi-solid formulations there may be mentioned, for example, poly-alkylene glycols, vaseline and other cream bases; for liquid formulations there may be mentioned, for example, water, oils of vegetable origin and low boiling solvents such as isopropanol, hydrogenated naphthalenes and the like. The pharmaceutical compositions containing the compounds of the present invention may be subjected to conventional pharmaceutical expedients such as sterilization and can contain conventional pharmaceutical excipients such as preservatives, stabilizing agents, emulsifying agents, salts for the adjustment of osmotic pressure and buffers. The compositions may also contain other therapeutically active materials. In pharmaceutical applications, the subject compounds and compositions may be administered to humans and animals by conventional methods, e.g., topically, orally, parenterally and the like. Parenteral administration includes intramuscular as well as subcutaneous and intravenous administration. Intravenous injection of imidazole-type anti-fungals has been demonstrated to be effective in the treatment of systemic mycoses (see for example, Drugs, 9, pp. 419–420, 1975, which describes the intravenous administration of miconazole, i.e. 1-[2,4-dichloro-$\beta$-(2',4'-dichlorobenzyloxy)phenethyl]-imidazole nitrate, to patients with systemic candidiasis). Topical application is the preferred method of administration for pharmaceutical applications. For such treatment, an area having an existing fungal, bacterial or protozoal growth, or to be protected against attack by fungi, bacteria or protozoa, may be treated with the subject compounds or compositions by, for example, dusing, sprinkling, spraying, rinsing, brushing, dipping, smearing, coating, impregnating and the like. Topical pharmaceutical compositions containing the compounds of the present invention exhibit anti-fungal anti-bacterial and anti-protozoal activity over a wide range of concentration, for example, from about 0.1 to 10.0% by weight of the composition. In any event, the composition to be administered will contain a quantity of the subject compound in an amount effective for relief or prevention of the specific condition being treated.

The pharmaceutical compositions hereof typically comprise one or more subject compounds of Formula (I) and a pharmaceutically acceptable, non-toxic carrier, and are preferably formulated in unit dosage form to facilitate administration (unit dosage being the amount of active ingredient administered on one occasion).

In general, or systemic (e.g., oral or parenteral) administration it is expedient to administer the active ingredient in amounts between about 1 and 100 mg./kg. body weight per day, preferably between about 5 and 50 mg./kg. body weight per day, preferably distributed over several applications (e.g., in 3 individual doses) in order to achieve most effective results. For localized (e.g. topical) administration, however, proportionately less of the active ingredient is required.

The exact regimen for pharmaceutical administration of the compounds and compositions disclosed herein will necessarily be dependent upon the needs of the individual subject being treated, the type of treatment, e.g., whether preventative or curative, the type of organism involved and, of course, the judgment of the attending practitioner.

In agricultural applications, the subject compounds may be applied directly to plants (e.g., seeds, foliage) or to soil. For example, compounds of the present invention may be applied to seeds alone or in admixture with a powdered solid carrier. Typical powdered carriers are the various mineral silicates, e.g., mica, talc, pyrophyllite, and clays. The subject compounds may also be applied to the seeds in admixture with a conventional surface-active wetting agent with or without additional solid carrier. Surface-active wetting agents that can be used are any of the conventional anionic, non-anionic or cationic types. As a soil treatment for fungi and the like, the subject compounds can be applied as a dust in admixture with sand, soil or a powdered solid carrier such as a mineral silicate with or without additional surface-active agent, or the subject compounds can be applied as an aqueous spray optionally containing a surface-active dispersing agent and a powdered solid carrier. As a foliage treatment, the subject compounds may be applied to growing plants as an aqueous spray which contains a surface-active dispersing agent with or without a powdered solid carrier and hydrocarbon solvents.

In industrial applications, the subject compounds may be used to control bacterial and fungi by contacting the pathogens with the compounds in any known manner. Materials capable of supporting bacteria and fungi may be protected by contacting, mixing or impregnating these materials with the subject compounds. In order to increase their effect, the subject compounds may be combined with other pesticidal control agents such as fungicides, bactericides, insecticides, miticides and the like. A particularly important industrial/agricultural use for the subject compounds of the present invention is as a food preservative against bacteria and fungi which cause deterioration and spoilage of foods.

The compounds of formula (I) may be considered to consist of two subclasses, those of formulas (Ia) and (Ib) shown below

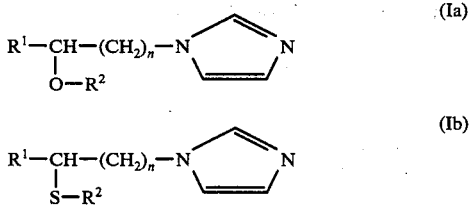

wherein $R^1$, $R^2$, and $n$ are as defined above.

Both groups of compounds may be prepared from common intermediates having a free hydroxyl group which is then converted to the ether or thioether, as the case may be, and which may be prepared by a variety of methods, depending upon the length of the $(CH_2)_n$ chain, i.e., the value of n.

One preferred subgenus of compounds of formula I are those wherein n is 1, 2 or 3.

Within this subgenus one group of preferrred compounds are those wherein $R^1$ is substituted or unsubstituted phenethyl, phenylpropyl or styryl, with compounds wherein n is 1 being most preferred. Within the above group (n is 1, 2 or 3), preferred compounds are those wherein $R^1$ is halo-substituted phenethyl or styryl. Halo substitution at the 4-position is preferred and, when there is more than one halo substituent, it is preferred that all halo groups be the same, most preferably chloro. Particularly preferred is 4-chloro substitution. Within the above group of compounds, preferred $R^2$ groups are substituted or unsubstituted phenyl or benzyl, most preferably halo-substituted phenyl or benzyl. One particularly preferred sub-group of compounds are those wherein $R^2$ is phenyl having a halo substituent in the ortho position. When there is more than one halo substituent it is preferred that all halo groups be the same, most preferably chloro. Preferred chloro substitution patterns for $R^2$ are 2,3-, 2,4-, 2,5-, 2,6-, 2-, 2,4,5- and 2,4,6-, especially 2,4-dichloro, 2,5-dichloro, 2,6-dichloro and 2-chloro. When $R^2$ is halo substituted phenyl it is preferred that X be sulfur. Another preferred sub-group of compounds are those wherein $R^2$ is halo substituted benzyl, most preferably chloro-substituted benzyl. Especially preferred are 2-chloro, 4-chloro, 2,4-dichloro and 2,6-dichlorobenzyl.

Another preferred group of compounds within the above mentioned subgenus are those wherein n is 2 or 3 and $R^1$ is phenyl, benzyl or halo substituted phenyl or benzyl, preferably 4-chloro-, 4-bromo-, 4-fluoro-, 2,4-dichloro-, 2,4-difluoro- or 2,4-dibromo-substituted and $R^2$ is independently phenyl or benzyl, or halo (preferably chloro)-substituted derivatives thereof (preferably those having 2-, 4-, 2,4-, 2,5-, or 2,6-substitution. Within this group of compounds of a first sub-group of compounds are those wherein $R^1$ is phenyl or halo-substituted phenyl, and a second sub-group of compounds are those wherein $R^1$ is benzyl or halo-substituted benzyl.

For all the above described preferred groups of compounds of Formula I, most preferred compounds have, for each of $R^1$ and $R^2$, no more than 2 substituents except when all substituents for $R^1$ and/or $R^2$ are halo.

As mentioned above, compounds of Formula (I) may be prepared by forming an ether or thioether from a suitable alcohol of formula (II)

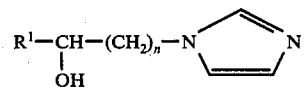

wherein $R^1$ and $n$ are as defined above. Compounds of formula (II) may be prepared by a variety of rection sequences, depending on the size of n.

For example, when $n$ is 1, certain compounds of formula (IIa) may be prepared by reaction scheme A shown below.

Reaction Scheme A

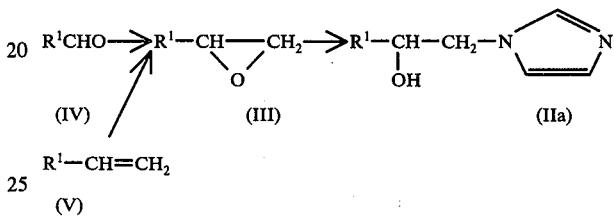

In this reaction scheme the imidazole alcohol of formula (IIa) is formed by opening of a terminal epoxide of formula (III) with imidazole. This reaction is generaly carried out using at least one mole and preferably an excess of imidazole relative to epoxide. The reaction may either be carried out in the absence of solvent or, preferably, in an inert organic solvent, for example, a solvent such as dimethylformamide, hexamethylphosphoramide, acetonitrile, and the like. The temperature normally employed for such epoxide opening is in the range of from about −20° to about 100° C. most preferably from about 20° to about 60° C.

Epoxides of formula (III), insofar as they may not be known or readily available, may be prepared by a variety of well known methods, for example epoxidation of a terminal olefin (e.g., (V)) with, for example, a peracid, or by reaction of an aldehyde having one fewer carbon atoms (e.g., (IV)) with the ylide prepared from trimethylsulfoxonium iodide as described, for example, in *J. Am. Chem. Soc.*, 84, p. 867 (1962); ibid, 87, p. 1353 (1965).

Another reaction scheme for preparing certain compounds of formula (IIa) is shown in reaction scheme B presented below Reaction Scheme B

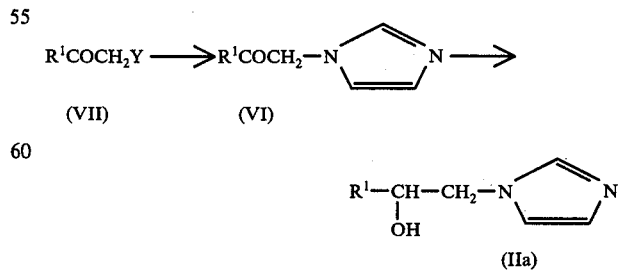

wherein Y is chloro or bromo.

In this reaction scheme the hydroxy compound of formula (IIa) is prepared by reduction of the corresponding ketone (VI), which in turn is prepared by reaction of an α-halo ketone (VII) with imidazole.

α-Halo ketones are generally available, or may be readily prepared by, for example, halogenation of the corresponding methyl ketone. When $R^1$ is styryl or substituted styryl, a particularly useful method of bromination is described in *Tetrahedron*, 29, p. 1625 (1973) and *Can. J. Chem.* 47, p. 706 (1969).

The α-halo ketone is contacted with imidazole in an inert organic solvent to afford the keto imidazole of formula (VI). The reaction is carried out utilizing at least a molar amount and, preferably, an excess of imidazole relative to halo ketone. The reaction may be carried out in the absence of solvent or, preferably, in an inert organic solvent such as for example dimethylformamide, hexamethylphosphoramide, acetonitrile, and the like. The reaction is suitably carried out at a temperature initially between about −10° and 100° C. most preferably between about 0° and 25° C.

In the next step the keto imidazole of formula (VI) is reduced to the hydroxy imidazole of formula (IIa) utilizing a conventional metal hydride reducing agent such as, for example, sodium borohydride. The reaction is suitably carried out in an alcoholic solvent such as, for example, methanol or ethanol at a reduced temperature, for example, between about −10° and +25° C., most preferably about 0° C.

When n is 2 compounds of formula (IIb) may be prepared according to a variety of synthetic methods. One convenient method for the preparation of certain compounds of formula (IIb) is shown in reaction scheme C presented below.

Reaction Scheme C

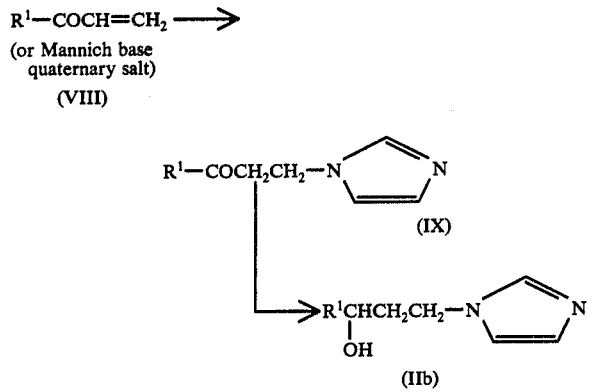

This scheme involves the reaction of imidazole with a vinyl ketone of formula (VIII) (or Mannich base quaternary intermediate) followed by reduction of the resulting keto imidazole of formula (IX) to the hydroxy imidazole of formula (IIb).

Vinyl ketones of formula (VIII), insofar as they may not be known or generally available, may be prepared by a variety of methods well known in the synthetic organic chemistry art, for example, by the addition of vinyl lithium to the corresponding carboxylic acid; by the addition of vinyl lithium to the corresponding aldehyde followed by oxidation of the allylic alcohol thus produced to the vinyl ketone (e.g., *J. Chem. Soc. (C)*, 1966, p. 1972; *J. Chem. Soc. (London)*, 1956, p. 3070); or by Mannich reaction of the corresponding methyl ketone, quaternization and elimination.

The first step of the conversion, the reaction of vinyl ketone of formula (VIII) to keto imidazole of formula (IX), is accomplished by contacting the vinyl ketone (or a Mannich quaternary base precursor) with imidazole in an inert organic solvent. The reaction is conveniently carried out utilizing at least a molar amount, and preferably an excess, of imidazole relative to vinyl ketone or Mannich quaternary base in an inert organic solvent, for example, diethyl ether, dichloromethane or dimethylformamide, at a temperature between about 0° and 40° C. preferably about ambient temperature.

The reduction of the keto imidazole of formula (IX) to the hydroxy imidazole of formula (IIb) is carried out in the same manner as described above for the conversion of compound of formula (VI) to that of formula (IIa).

When n is 2 (or greater) certain compounds of formula (II) are conveniently prepared as illustrated in reaction scheme D presented below Reaction Scheme D

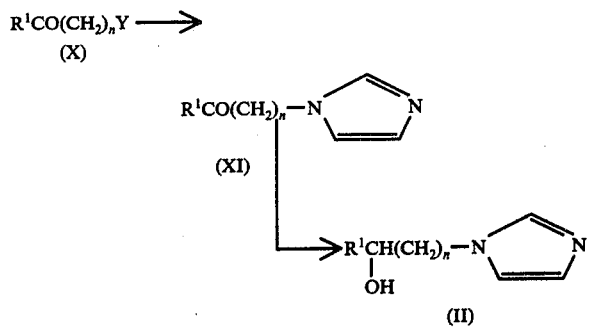

wherein Y is chloro or bromo.

In this reaction scheme an ω-halo (preferably chloro) ketone of the formula (X) is converted to the corresponding keto imidazole of formula (XI) and then to the hydroxy imidazole of the formula (II).

The starting ω-halo ketones, insofar as they may not be known or generally available, may be suitably prepared by the well known Friedel-Crafts reaction involving the aromatic hydrocarbon $R^1H$ and an ω-halo acylhalide.

The conversion from compound (X) to compound (XI) is carried out using imidazole in the same manner as described above for the conversion of (VII)→(VI). When n is 3 or greater, the reaction temperature is between about 0 and 100° C., preferably between 25° and 80° C.

The reduction of the keto imidazole of formula (XI) to the hydroxy imidazole of formula (II) is carried out as previously described for the conversion of (VI)→(IIa).

Certain compounds of formula (IIc) may also be prepared by an alternate procedure depicted in reaction scheme E Reaction Scheme E

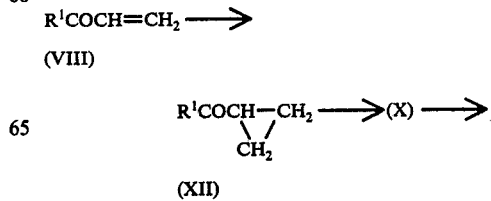

-continued
Reaction Scheme E

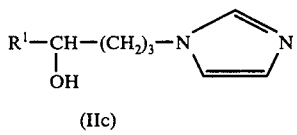

(IIc)

involving the conversion of the previously described vinyl ketone of the formula (VIII) to the corresponding cyclopropyl ketone of the formula (XII), followed by conversion to the γ-halo ketone of formula (X), $n=3$, and then, as described above, to the hydroxy imidazole of formula (IIc).

The cyclopropanation of the vinyl ketone of formula (VIII) may be accomplished by methods known per se, for example as disclosed in *J. Am. Chem. Soc.*, 87, p. 1353 (1965). The resulting cyclopropyl ketone is then opened to afford the γ-halo ketone by treatment with a hydrohalic acid such as, for example, hydrobromic acid.

Certain compounds of formula (II) may also be prepared according to reaction scheme F below Reaction Scheme F $R^1CHO + CH_2=CH-(CH_2)_{n-2}Y \longrightarrow$
(IV)           (XIII)

$R^1CO(CH_2)_nY \longrightarrow$
(X)

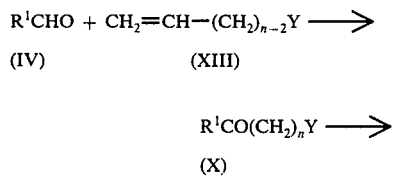

(XI)

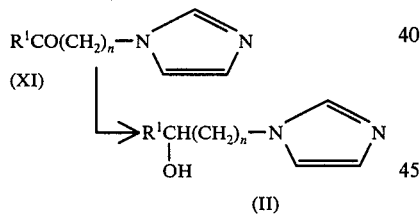

(II)

wherein Y is chloro or bromo.

This reaction scheme is particularly useful for preparing compounds wherein n is 4 or greater, but may also be used to prepare compounds where n is 2 or 3. In this scheme, the previously described aldehyde of formula (IV) is reacted with an ω-halo terminal alkene of formula (XIII), readily prepared, for example, by halogenation of the corresponding alcohol, in a free radical addition reaction to afford the previously described halo ketone of formula (X), which is then converted as previously described through the keto imidazole of formula (XI), to the hydroxy imidazole of formula (II). The conversion (IV) + (XIII)→(X) is conveniently carried out using a free radical source such as, for example, diacetyl peroxide, di-tert-butyl peroxide, dibenzoyl peroxide, azobisisobutyronitrile; or photochemically, at a temperature between about 50° and 150° C., most preferably between about 60° and 80° C., using an excess of the aldehyde as a solvent medium.

Certain compounds of formula (III) may be also prepared as demonstrated below in reaction scheme G Reaction Scheme G $R^1COY + CH_2=CH-(CH_2)_{n-2}-Y$
(XIV)    (XIII)

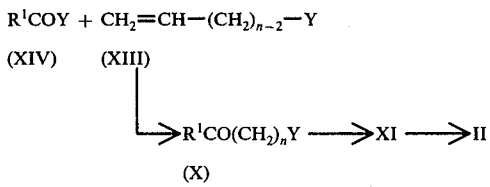

wherein Y is chloro or bromo.

This reaction scheme is conveniently utilized where compounds having n equal to or greater than 4 are desired.

In this reaction scheme an acid halide of formula (XIV), readily prepared from the corresponding carboxylic acid, is reacted with the previously described ω-halo terminal alkene of formula (XIII) to afford the halo ketone of the formula (X), which is then converted, as shown above, to the hydroxy imidazole of formula (II). The addition reaction between compounds of formulas (XIV) and (XIII) is conveniently carried out under conditions as described in G. Olah, "Friedel Crafts and Related Reactions", Vol. 3, Part 2, Interscience Publishers, New York, (1964).

In yet another reaction sequence certain compounds of formula (II) wherein n is 1 or greater may be prepared. This is illustrated below in reaction scheme H Reaction Scheme H $R^0-CH=CH_2 +$
(XV)

$YCO(CH_2)_nY \longrightarrow R^1CO(CH_2)_ny$
(XVI)              (X)

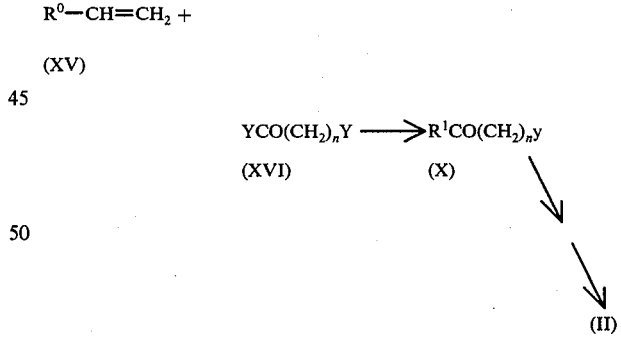

(II)

wherein $R^1$ is $R^oCH_2CH_2$ and Y is chloro or bromo.

In this scheme the ω-halo ketone of formula (X), described above, is prepared starting with a terminal olefin of formula (XV) and an ω-halo acyl halide of formula (XVI), readily prepared, for example, from the corresponding hydroxyacid. This reaction is carried out under the conditions described above for Reaction Scheme G.

In reaction scheme I shown below there are illustrated alternative methods for preparing certain compounds of formula (II) wherein n is 1, Reaction Scheme I

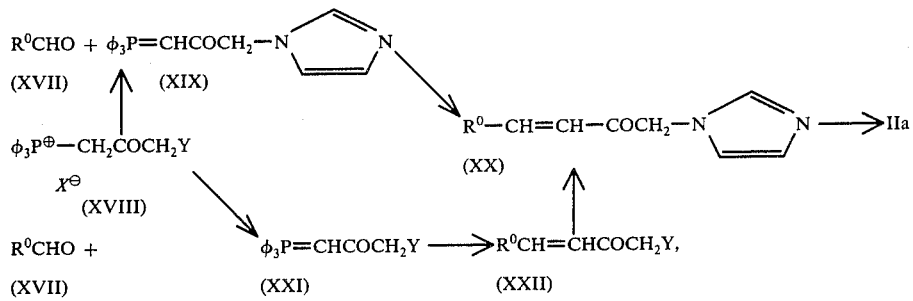

$R^1$ is $R^0$—CH=CH— or $R^0CH_2CH_2$— and Y is chloro or bromo.

In this scheme an aldehyde of formula (XVII) is reacted, in a Wittig reaction, with an ylide of formula (XIX) or (XXI) to afford the corresponding olefin of formula (XX) or (XXII). The ylide (XXI) is formed, according to methods known per se, from the corresponding phosphonium salt (XVIII), prepared in turn from triphenylphosphine and the corresponding dihalo acetone. To form the ylide of formula (XIX) the phosphonium salt is reacted with an excess of imidazole, in an inert organic solvent such as acetonitrile, dimethylformamide at a temperature between about 25° and 100° C., preferaly between about 50° and 80° C., thus affording the imidazole substituted ylide of formula (XIX) which, upon reaction with the aldehyde of formula (XVII) under standard Wittig conditions, (e.g., in acetonitrile at 80° C.) affords the unsaturated keto imidazole of formula (XX).

Alternatively, reaction of the aldehyde of formula (XVII) with the ylide of formula (XXI), prepared in the normal manner from phosphonium salt (XVIII) by treatment with a base such as an alkali metal carbonate, affords the halo unsaturated ketone of formula (XXII). This compound may then be converted to the corresponding imidazole compound of formula (XX) by treatment with imidazole as described above the conversion (VII)→ (VI). Reduction of the keto group of compound (XX) affords the hydroxy imidazole of formula (IIa). The double bond adjacent to the hydroxy moiety may be hydrogenated to afford a compound of formula (IIa) having a phenyl lower alkyl or substituted phenyl lower alkaly moiety as $R^1$. Such hydrogenation may be carried out using standard conditions, for example, using a palladium on charcoal catalyst in a solvent such as methanol. Alternatively, hydrogenation may be performed prior to reduction of the ketone.

The compounds of formula (II) are converted to the final products of formula (I) wherein X is O and $R^2$ is substituted or unsubstituted phenyl straight chain lower alkyl or phenyl straight chain lower alkenyl, by O-alkylation with the appropriate $R^2Y$ wherein Y is a leaving group such as halide (chloride, bromide or iodide) or sulfonate ester (e.g., p-toluenesulfonate or methanesulfonate).

The alkylation is carried out by converting the hydroxy group of the compound of formula (II) to its alkali metal salt by treatment with a strong base such as, for example, an alkali metal hydride such as sodium hydride; and alkali metal amide such as sodium amide or potassium amide; and the like. This is preferably done in an inert organic solvent such as, for example, dimethylformamide, hexamethylphosphoramide, tetrahydrofuran, and the like. The alkali metal salt is then contacted with the $R^2Y$, preferably in the same solvent system, at a temperature between about 0° and 80° C., most preferably between about 0° and 60° C.

Compounds of formula (I) wherein $R^2$ is substituted or unsubstituted phenyl (i.e., phenolic ethers or thioethers) may be prepared from the compounds of formula (II) by a two-step sequence involving conversion of the hydroxy group to a suitable leaving group such as a halide (e.g., a chloride or bromide) or a sulfonate ester (e.g., methanesulfonate or p-toluenesulfonate) which is then reacted with a metal salt of the corresponding phenol $R^2OH$ or thiophenol $R^2SH$.

The conversion from the alcohol to the halide or sulfonate ester is carried out by means well known in the art. For example, the alcohol may be halogenated using a halogenating agent such as thionyl chloride or thionyl bromide, either neat, or in an inert organic solvent such as dichloromethane or chloroform, at a temperature between about 0° and 80° C., preferably between about 20° and 80° C. The halogenation reaction may be carried out in the presence of a molar equivalent of a base (e.g., pyridine) if desired. Alternate halogenation procedures include, for example, the use of triphenylphosphine with either carbon tetrachloride, carbon tetrabromide, or N-chloro (or N-bromo) succinimide. When utilizing thionyl chloride or thionyl bromide without the use of added base, the hydrochloride or hydrobromide salt of the corresponding halo compound is produced. This salt may be neutralized (e.g., with potassium carbonate) prior to its use in the alkylation step, or the salt may be used directly if excess phenol or thiophenol salt is utilized.

Sulfonate esters may be prepared by the standard procedure of treating the alcohol with an excess of, for example, methanesulfonyl chloride or p-toluenesulfonyl chloride, in the presence of a base, for example pyridine or triethylamine. This reaction is carried out at a temperature from about −20° to +50° C., preferably between about 0° and 20° C.

The halide or sulfonate ester prepared as described above, is then treated with a metal salt, preferably an alkali metal salt such as the sodium or potassium salt, of the corresponding phenol or thiophenol, in the presence of an inert organic solvent solvent such as acetone, methanol, and the like, at a temperature of about 20° to about 80° C. If desired, the metal salt of the phenol or thiophenol may be preformed prior to addition of the halide.

Compounds of formula (I) wherein X is S and $R^2$ is substituted or unsubstituted phenyl straight chain lower alkyl or phenyl straight chain lower alkenyl, may be prepared by reacting the above mentioned halide or sulfonate ester with the metal salt, preferably an alkali metal salt such as the sodium or potassium salt, of a thiol R²SH. This reaction is carried out in an inert organic solvent such as for example, tetrahydrofuran, diethylether, methanol, and the like. The salt is formed with a strong base such as for example, sodium hydride, sodium amide, sodium methoxide and the like, at a temperature between about 20° and 80° C.

Compounds of formula (I) wherein $n$ is 1, X is S and R¹ is substituted or unsubstituted phenyl straight chain lower alkyl may also be prepared as depicted in reaction scheme J below.

Reaction Scheme J

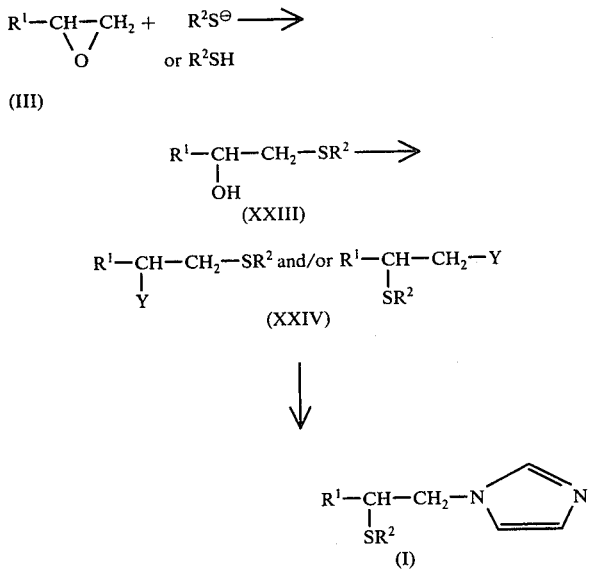

wherein Y is a leaving group.

In this scheme the epoxide of formula (III) described earlier, is open with a thiol or thiophenol or a metal salt thereof, to afford the compound of formula (XXIII). This reaction is carried out utilizing, preferably, an alkali metal salt of the thiol or thiophenol, most preferably the sodium salt, in an inert organic solvent such as, for example, tetrahydrofuran or acetone at a temperature of between about 0° and 67° C., or using the free thiol or thiophenol in the presence of an acid catalyst, e.g., perchloric acid, under similar conditions.

In the next step the hydroxy group of the compound of formula (XXIII) is converted to a leaving group such as a halide (e.g., chloro or bromo) or sulfonate ester (e.g., p-toluenesulfonate or methanesulfonate) by treatment with, e.g., a halogenating agent such as, for example, thionyl chloride, neat, or preferably in an inert solvent such as dichloromethane, or with, for example, p-toluenesulfonyl chloride, in a solvent such as pyridine. The product of formula (XXIV) may exist in either or both forms depicted, and may be interconvertible through an episulfonium intermediate.

In the final step, the compound of formula (XXIV) is converted to the final product of formula (I) by treatment with imidazole. This reaction is carried out in an inert organic solvent such as for example acetonitrile, dimethylformamide, and the like, at a temperature of about 0° to about 80° C.

Alternatively, certain compounds of formula (I) may be formed, in a final step, by hydrogenation of a compound of the formula

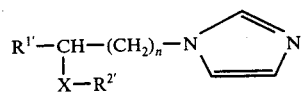

or an acid addition salt thereof wherein R¹' and R²' are identical with R¹ and R², respectively, except that R¹' and/or R²' contains aliphatic olefinic unsaturation, i.e., wherein R¹' and/or R²' is a substituted or unsubstituted phenyl lower alkenyl group. Such hydrogenation may be carried out using conditions well known in the art. For example, the hydrogenation may be carried out at about atmospheric pressure or at higher pressure, and at temperatures from about 0° to about 100° C., in the presence of a suitable supported, unsupported or soluble metal catalyst such as palladium, platinum or tris (triphenylphosphine) chlororhodium, in an inert solvent such as benzene, acetone, methanol, and the like, for a time sufficient to allow the uptake of the required amount of hydrogen.

The subject compounds of the instant invention can be isolated as free bases; however, since many of the compounds in base form are oils, it is more convenient to isolate and characterize the compounds as acid addition salts. These salts are prepared in the usual manner, i.e., by reaction of the base compound with a suitable inorganic or organic acid, described above. Salts formed with dibasic acids (e.g., oxalic acid) may contain one or two molecules of base per molecule of acid. All oxalates described herein contain one molecule of oxalic acid per molecule of imidazole base. If desired, the salts can be readily converted to the free base form by treatment with alkali, such as potassium carbonate, sodium carbonate or sodium or potassium hydroxide.

For following specific examples are illustrative of the present invention and should not be considered as limitative thereof in any manner.

PREPARATION 1

This preparation illustrates the process in reaction scheme A.

3-Phenylpropionaldehyde (26.8 g.) is added under nitrogen to the ylide prepared from trimethylsulfoxonium iodide (48.4g.) and sodium hydride (55% dispersion in oil; 9.6 g.) in dry dimethylsulfoxide (200 ml.), according to the procedure in *Journal of the American Chemical Society*, Vol. 84, page 867 (1962) and Vol. 87, page 1353 (1965). After one hour, the solution was poured into 1 liter of water and the product extracted with ether (3 × 300 ml.). The extract was washed with water (2 × 150 ml.) dried (MgSO₄) and evaporated to give an oil, 1,2-epoxy-4-phenylbutane, used directly in the next step.

The oil from above in 50 ml. of dimethylformamide was treated with imidazole (70 g.) and the mixture stirred at 40° C. overnight. The resulting solution was poured into a mixture of 700 ml. water and 200 ml. hexane, stirred until crystallization was complete, and the product was filtered off as buff granules (28.2 g.). Recrystallization from ethyl acetate gave 1-(2-hydroxy-4-phenylbutyl)imidazole as colorless crystals, m.p. 106°-107° C.

Similarly, proceeding as above, substituting the appropriate aldehyde for 3-phenylpropionaldehyde, there may be prepared, for example, the following compounds of formula (IIa):

1-[2-hydroxy-4-(4-chlorophenyl)butyl]imidazole

1-[2-hydroxy-4-(2,4-dichlorophenyl)butyl]imidazole
1-[2-hydroxy-4-(4-tert-butylphenyl)butyl]imidazole
1-[2-hydroxy-4-(4-fluorophenyl)butyl]imidazole
1-[2-hydroxy-4-(4-bromophenyl)butyl]imidazole
1-[2-hydroxy-4-(4-trifluoromethylphenyl)butyl]imidazole
1-2-hydroxy-5-(4-chlorophenyl)pentyl]imidazole
and
1-[2-hydroxy-4-(2,4-dimethylphenyl)butyl]imidazole

PREPARATION 2

This preparation illustrates the process in reaction scheme B.

Bromomethyl styryl ketone (22.5 g., reference Tetrahedron, Vol. 29, page 1625-8, 1973) in a few ml. of dimethylformamide was added dropwise to a well-stirred, ice cooled solution of imidazole (35 g.) in dimethylformamide (25 ml.), keeping the temperature below 13° C. The mixture was stirred for three hours at 0° C., then overnight at 25° C., and poured into 1 liter of water. The solution was extracted successively with benzene (600 ml.) and ether (600 ml.) and the combined extracts were dried (MgSO$_4$) and evaporated. Addition of benzene to the residue gave lemon-yellow granules (12 g.). Treatment of a solution of this product in methanol with ethereal hydrogen chloride, removal of the solvent and trituration of the residue with ethyl acetate (100 ml.) gave 5.75 g. of 1-(4-phenylbut-3-en-2-onyl) imidazole hydrochloride as a white solid, m.p. 208°-210° C.

The above ketone (5.50 g.) in 50 ml. of methanol at 0° C. was treated with stirring with excess sodium borohydride. When the reaction was complete, the solvent was evaporated and the residue treated with ice-cold water (10 ml.). Filtration and washing with a small quantity of ice water gave an off-white powder (5.40 g.), recrystallized from benzene to give 1(2-hydroxy-4-phenylbut-3-enyl)imidazole (5.20 g.), m.p. 125°-127.5° C.

Similarly proceeding as above, substituting the appropriate halo ketone for bromomethyl styryl ketone, there may be prepared, for example, the following compounds of formula (IIa):
1-(2-hydroxy-3-phenylpropyl)imidazole
1-[2-hydroxy-3-(4-chlorophenyl)propyl]imidazole
and
1-[2-hydroxy-4-(4-chlorophenyl)but-3-enyl]imidazole

PREPARATION 3

This preparation illustrates the process in reaction scheme C.

A. 7.0 g. of 2,4-dichlorophenyl vinyl ketone (prepared by Jones oxidation of 2,4-dichlorophenyl vinyl carbinol using the general method described in *J. Chem Soc.* (C), 1966, p. 1972) in 350 ml. of anhydrous ether was treated with 3.5 g. of imidazole, the solution stirred overnight and then washed with water (3 × 30 ml.). The solution is dried (MgSO$_4$) and evaporated to give 2,4-dichloro-β-(1-imidazolyl)propiophenone as an amber gum (8.65 g.). The hydrochloride salt may be precipitated from ether and recrystallized from methanol/acetone as colorless rods, m.p. 105.5°-110° C.

B. 13.1 g. of 2,4-dichlorobenzoylethyl trimethylammonium iodide (prepared by Mannich reaction of 2,4-dichloroacetophenone with paraformaldehyde and dimethylamine hydrochloride, followed by quaternization with methyl iodide in ether) and 12 g. of imidazole in dimethylformamide (50 ml.) was stirred overnight at room temperature and poured into 500 ml. of water. The product was extracted with ether (3 × 300 ml.), the extracts washed with water (3 × 75 ml.) and dried. Addition of ethereal hydrogen chloride precipitated the hydrochloride of 2,4-dichloro-β-(1-imidazolyl) propiophenone, which was recrystallized from methanol/acetone, m.p. 105°-109° C.

C. The ketone prepared in part A or part B above may be reduced to the corresponding alcohol, 1-[3-hydroxy-3-(2,4-dichlorophenyl)propyl]imidazole, m.p. 112°-114.5° C. following the procedure described in Preparation 2.

D. Similarly proceeding as above, substituting the appropriate vinyl ketone or Mannich quaternary salt for those indicated in Part A or B, there may be prepared, for example, the following compounds of formula (IIb):

1-[3-hydroxy-3-(4-chlorophenyl)propyl]imidazole, m.p. 95°-100° C.
1-[3-hydroxy-3-(4-tert-butylphenyl)propyl]imidazole, m.p. 139.5°-140.5° C.
1-[3-hydroxy-3-(4-fluorophenyl)propyl]imidazole, m.p. 104.5°-110° C.
1-[3-hydroxy-3-(2,4-dimethylphenyl)propyl]imidazole
1-(3-hydroxy-4-phenylbutyl)imidazole
1-[3-hydroxy-4-(4-chlorophenyl)butyl]imidazole
1-[3-hydroxy-4-(4-methylphenyl)butyl]imidazole
1-[3-hydroxy-5-(4-chlorophenyl)pentyl)imidazole
and
1-[3-hydroxy-3-(2-trifluoromethylphenyl)propyl]imidazole
1-[2-hydroxy-3-(2,4-dibromophenyl)propyl]imidazole
1-[3-hydroxy-3-(2,4-difluorophenyl)propyl]imidazole

PREPARATION 4

This preparation illustrates the process of reaction scheme D.

A. β-Chloropropiophenone (16.8 g.) and imidazole (35 g.) in dimethylformamide (25 ml.) were stirred at 0° C. for three hours and poured into 700 ml. water. The product was filtered off as buff flakes (15.9 g.) and recrystallized from cyclohexane as colorless flakes of β-(1-imidazolyl)propiophenone, m.p. 96°-99.5° C.

The above material (5.60 g.) in 70 ml. of methanol was treated at 0° C. with excess sodium borohydride. When the reaction was complete, the solvent was evaporated, 100 ml. of water was added and the product (4.90 g.) was filtered off. Recrystallization from ethyl acetate gave 1-(3-hydroxy-3-phenylpropyl)imidazole as colorless rods, m.p. 106.5°-108° C.

B. To a 0° C. slurry of 8.24 g. of imidazole in 15 ml. dry dimethylformamide was added 5.79 g. of p-t-butyl-γ-chlorobutyrophenone and the mixture was stirred overnight at room temperature, then one day at 60° C. The above solution was poured into 400 ml. of water and extracted three times with ethyl acetate. The combined extracts were washed with water, dried over magnesium sulfate and the solvent evaporated to afford 5.25 g. of 1-[4(4-t-butylphenyl)butan-4-onyl]imidazole as a golden oil.

To a 0° C. solution of 5.0 g. of the above ketone in 150 ml. of anhydrous methanol was added excess sodium borohydride, and the mixture stirred for one hour. After removal of the solvent, a small quantity of water was added and the mixture was extracted with ethyl acetate. The combined extracts were dried over magnesium sulfate and evaporated to afford 1[4-hydroxy-4-(4-t-butylphenyl)butyl]imidazole, which was converted to the oxalate salt and recrystallized from ethyl acetate/ethanol, m.p. 205°–207° C. (foaming).

Similarly, proceeding as above, substituting the appropriate haloketone for those indicated in part A or B, there may be prepared, for example, the first four compounds of formula (IIb) listed in Preparation 3, as well as the following compounds of formula (II):

1-[4-hydroxy-4-(4-chlorophenyl)butyl]imidazole
1-[4-hydroxy-4-(2,4-dichlorophenyl)butyl]imidazole
1-[4-hydroxy-4-(4-fluorophenyl)butyl]imidazole, m.p. 91.5°–94° C.
1-[4-hydroxy-4-(2,4-dimethylphenyl)butyl]imidazole
1-[4-hydroxy-4-(4-bromophenyl)butyl]imidazole, m.p. 113.5°–115° C.
1-(4-hydroxy-5-phenylpentyl)imidazole
1-[4-hydroxy-5-(4-chlorophenyl)pentyl]imidazole
1-[4-hydroxy-6-(4-chlorophenyl)hexyl]imidazole
1-(6-hydroxy-6-phenylhexyl)imidazole
1-[6-hydroxy-6-(4-chlorophenyl)hexyl]imidazole
1-[6-hydroxy-7-(4-chlorophenyl)heptyl]imidazole
1-(6-hydroxy-8-phenyloctyl)imidazole
1-(6-hydroxy-10-phenyldecyl)imidazole
1-(9-hydroxy-9-phenylnonyl)imidazole
1-[9-hydroxy-9-(4-chlorophenyl)nonyl]imidazole
1-[9-hydroxy-10-(4-chlorophenyl)decyl]imidazole
1-(9-hydroxy-11-phenylundecyl)imidazole
and
1-(9-hydroxy-13-phenyltridecyl)imidazole

PREPARATION 5

This preparation illustrates the process of reaction scheme I.

7.3 g. of chloroacetylmethyl triphenylphosphonium chloride and 7.3 g. of imidazole in acetonitrile (60 ml.) were stirred and heated at 80° C. for two days. The resulting solution was evaporated and the residue treated with water, extracted with benzene, and the extract washed with water, dried (MgSO₄) and evaporated. Recrystallization from ethyl acetate/cyclohexane afforded 1-imidazolylacetylmethylenetriphenylphosphorane, as colorless blades, m.p. 154.5°–158° C.

The above phosphorane (3.85 g.) and p-tolualdehyde (2.4 g.) were stirred in 30 ml. of acetonitrile and refluxed overnight. After evaporation to dryness, the residue was chromatographed on silica gel eluting with acetone/dichloromethane to afford 1-[4-(4-methylphenyl)-but-3-en-2-onyl]imidazole as a colorless solid.

This material was reduced with sodium borohydride, following the procedure in Preparation 2 to afford 1-[2-hydroxy-4(4-methylphenyl)but-3-enyl]imidazole.

In a similar manner, substituting benzaldehyde for p-tolualdehyde, there was prepared 1-(2-hydroxy-4-phenylbut-3-enyl) imidazole, m.p. 125°–127.5° C.

2.5 g. of this material in 30 ml. of methanol was hydrogenated at ambient temperature and pressure over a 10% palladium on charcoal catalyst. When the uptake of hydrogen ceased, the solution was filtered, and the residue was recrystallized from benzene/cyclohexane to give white microcrystals (2.37 g.) of 1-(2-hydroxy-4-phenylbutyl)imidazole, m.p. 108°–109.5° C.

Similarly proceeding as above, substituting the appropriate aldehyde for those indicated, there may be prepared, for example, the following compounds of formula (Ia):

1-[2-hydroxy-4-(4-chlorophenyl)but-3-enyl]imidazole
1-[2-hydroxy-4-(4-chlorophenyl)butyl]imidazole
1-[2-hydroxy-4-(2,4-dichlorophenyl)but-3-enyl]imidazole
1-[2-hydroxy-4-(2,4-dichlorophenyl)butyl]imidazole
1-[2-hydroxy-4-(4-tert-butylphenyl)but-3-enyl]imidazole
1-[2-hydroxy-4-(4-tert-butylphenyl)butyl]imidazole
1-[2-hydroxy-4-(4-fluorophenyl)but-3-enyl]imidazole
1-[2-hydroxy-4-(4-fluorophenyl)butyl]imidazole
1-[2-hydroxy-4-(2,4-dimethylphenyl)but-3-enyl]imidazole
and
1-[2-hydroxy-4-(2,4-dimethylphenyl)butyl]imidazole

EXAMPLE 1

A. A mixture of 430 mg. of 1-(2-hydroxy-4-phenylbutyl)imidazole and 96 mg. of sodium hydride (56% dispersion in mineral oil) in 3 ml. of dry hexamethylphosphoramide was stirred under nitrogen at room temperature for one hour and at 45° C. for one hour. After the evolution of hydrogen ceased, the solution was cooled in an ice bath and a solution of 430 mg. of 2,4-dichlorobenzyl chloride in 2 ml. hexamethylphosphoramide added dropwise keeping the temperature below 10° C. The solution was stirred for one hour at room temperature, 2 hours at 45° C. and let stand overnight. The resulting mixture was then poured into water, extracted with ether, the ether extracts washed with water, dried and evaporated. The oily product, 1-[2-(2,4-dichlorobenzyloxy)-4-phenylbutyl]imidazole, was converted to its nitrate salt by treatment of an ethereal solution with concentrated nitric acid, which salt was recrystallized from ethyl acetate as large colorless flakes, m.p. 121°–124° C.

B. trans-1-[2-Hydroxy-4-phenylbut-3-enyl]imidazole (430 mg.) in 5 ml. dry tetrahydrofuran was treated under nitrogen with stirring with 96 mg. of sodium hydride (56% dispersion in mineral oil) and the mixture heated under reflux for 30 minutes. After cooling in an ice bath the mixture was treated with stirring with 430 mg. of α,2,4-trichlorotoluene in 5 ml. tetrahydrofuran for 30 minutes at 0° C., one hour at 25° C. and overnight under reflux. The resulting mixture was evaporated to dryness, ether (150 ml.) added and the ether extract washed with water, dried over magnesium sulfate and evaporated to afford trans-1-[2-(2,4-dichlorobenzyloxy)-4-phenylbut-3-enyl]imidazole. The nitrate salt precipitated from ether and was crystallized from ethyl acetate, m.p. 133.5°–134.5° C. (foaming).

A solution of 1.00 g. of 1-(2-hydroxy-4-phenylbutyl) imidazole in 40 ml. of dichloromethane was treated with 1 ml. of thionyl chloride with stirring and the solution heated to gentle reflux for one hour. Evaporation to dryness afforded 1-(2-chloro-4-phenylbutyl) imidazole hydrochloride as a white solid.

The free base may be obtained for use in the subsequent alkylation steps, if desired, by shaking the hydrochloride in dichloromethane with excess aqueous potassium carbonate solution, washing the organic layer with water, drying over magnesium sulfate and evaporating to dryness.

EXAMPLE 3

600 Mg. of 1-(2-chloro-4-phenylbutyl) imidazole hydrochloride was added to a fully reacted mixture of 1.1 g. of 3,4-dichlorobenzylmercaptan and 400 mg. of 56% sodium hydride dispersion in mineral oil in 30 ml. of tetrahydrofuran. After stirring under reflux for 12 hours the solvent was evaporated under vacuum and 150 ml. of ether was added. The resulting mixture was washed twice with water and the ethereal solution dried and evaporated to afford 1-[2-(3,4-dichlorobenzylthio)-4-phenylbutyl]imidazole, as an oil. This material was converted to the oxalate salt by treatment of an ethereal solution wih oxalic acid in ether until precipitation was complete, which salt was recrystallized from acetone-/ethyl acetate as colorless flakes (660 mg.), m.p. 143.5°–146° C.

EXAMPLE 4

A mixture of 600 mg. of 1-(2-chloro-4-phenylbutyl-)imidazole hydrochloride, 1.2 g. of 3,4-dichlorothiophenol and 800 mg. of potassium carbonate in 40 ml. of acetone was stirred and refluxed for 4 hours. The solvent was evaporated under vacuum and 50 ml. of water was added. The resulting mixture was extracted with ether and the ether extract was washed with saturated sodium chloride solution, dried and evaporated to afford 1-[2-(3,4-dichlorophenylthio)-4-phenylbutyl]imidazole as an oil. This material was converted to the oxalate salt by treatment with oxalic acid in ether, which salt was recrystallized from acetone/ethyl acetate as colorless flakes (850 mg.), m.p. 145°–147° C.

EXAMPLE 5

1,2-Epoxy-4-phenylbutane (1.48 g.) in dry tetrahydrofuran (10 ml.). was added to the clear solution obtained from the reaction of 50 mg. of 56% sodium hydride dispersion in mineral oil with 2.25 g. of 3,4-dichlorobenzylmercaptan in 50 ml. of dry tetrahydrofuran.

After stirring for four hours at 60° C. the solvent was removed, the residue treated with water and extracted with ether. The ether extract was dried and evaporated to afford a colorless oil.

The above oil in 30 ml dichloromethane was treated with 2 ml. of thionyl chloride at room temperature for 30 minutes, and the solution evaporated to dryness. The residue was treated with 4 g. of imidazole and 15 ml. of acetonitrile and stirred overnight at room temperature and for one day at 50° C. The solvent was evaporated and after the addition of 50 ml. water the residue was extracted with ether. The ether extract was washed with water, dried and evaporated to afford 1-[2-(3,4-dichlorobenzylthio)-4-phenylbutyl]imidazole as an oil, which was further characterized as its oxalate salt, m.p. 143.5°–146° C.

EXAMPLE 6

Following the procedures in Preparations 1, 2 or 5, and Examples 1; 2,3; 2,4; or 5, using equivalent amounts of the appropriate starting materials, there may be obtained the following compounds. Where indicated, the compounds may be further characterized by conversion to the indicated acid addition salt.

1-[2-(3,4-dichlorobenzylthio)-3-phenylpropyl]imidazole
1-[2-(4-chlorophenylthio)-3-phenylpropyl]imidazole
1-[2-(2,4-dichlorophenoxy)-3-phenylpropyl]imidazole
1-[2-(3,4,5-trichlorophenylthio)-3-phenylpropyl]imidazole
1-[2-(2,4-dichlorobenzyl)-3-(4-chlorophenyl)propyl]imidazole
1-[2-(4-fluorophenylthio)-3-(4-chlorophenyl)propyl]imidazole
1-[2-(4-tert-butylphenoxy)-3-(4-chlorophenyl)propyl]imidazole
1-[2-(3,4-dichlorophenylpropylthio)-3-(4-chlorophenyl)propyl]imidazole
1-[2-(2,4-dichlorobenzylthio)-4-phenylbutyl]imidazole
1-[2-(3,4-dichlorobenzyloxy)-4-phenylbutyl]imidazole
1-[2-(3,4-dichlorophenoxy)-4-phenylbutyl]imidazole
1-[2-(2,3,4,5,6-pentachlorophenylthio)-4-phenylbutyl]imidazole
1-[2-(4-bromobenzylthio)-4-phenylbutyl]imidazole
1-[2-(4-fluorophenoxy)-4-phenylbutyl]imidazole
1-[2-(4-methylphenylthio)-4-phenylbutyl]imidazole
1-[2-cinnamyloxy-4-phenylbutyl]imidazole
1-[2-(4-chlorophenylthio)-4-(4-chlorophenyl)butyl]imidazole-nitrate salt, m.p. 116°–119° C.
1-[2-(4-chlorophenoxy)-4-(4-chlorophenyl)butyl]imidazole
1-[2-(4-chlorobenzylthio)-4-(4-chlorophenyl)butyl]imidazole-oxalate salt, m.p. 143°–144° C; nitrate salt, m.p. 120°–121° C
1-[2-(4-chlorobenzyloxy)-4-(4-chlorophenyl)butyl]imidazole
1-[2-(2,4-dichlorobenzyloxy)-4-(4-chlorophenyl)butyl]imidazole - nitrate salt, m.p. 152°–153.5° C
1-[2-(2,4-dichlorobenzylthio)-4-(4-chlorophenyl)butyl]imidazole - nitrate salt, m.p. 101°–108° C.
1-[2-(3,4-dichlorobenzyloxy)-4-(4-chlorophenyl)butyl]imidazole
1-[2-(3,4-dichlorobenzylthio)-4-(4-chlorophenyl)butyl]imidazole - nitrate salt, m.p. 87.5°–89.5° C.
1-[2-(3,4-dichlorobenzylthio)-4-(4-chlorophenyl)butyl]imidazole
1-[2-(2,4,5-trichlorophenylthio)-4-(4-chlorophenyl)butyl]imidazole
1-[2-cinnamyloxy-4-(4-chlorophenyl)butyl]imidazole
1-[2-(2,4-dichlorophenylthio)-4-(4-chlorophenyl)butyl]imidazole — nitrate salt, m.p. 115°–116° C
1-[2-(4-chlorocinnamyloxy)-4-(4-chlorophenyl)butyl]imidazole
1-[2-(4-fluorocinnamylthio)-4-(4-chlorophenyl)butyl]imidazole
1-[2-(4-trifluoromethylphenylthio)-4-(4-chlorophenyl)butyl]imidazole
1-[2-(4-chloro-3-trifluoromethylphenylthio)-4-(4-chlorophenyl)butyl]imidazole
1-[2-(4-trifluoromethylbenzyloxy)-4-(4-chlorophenyl)butyl]imidazole
1-[2-(benzylthio)-4-(2,4-dichlorophenyl)butyl]imidazole
1-[2-(4-chlorobenzyloxy)-4-(2,4-dichlorophenyl)butyl]imidazole
1-[2-(2,4-dichlorobenzylthio)-4-(2,4-dichlorophenyl)butyl]imidazole
1-[2-(3,4-dichlorobenzylthio)-4-(2,4-dichlorophenyl)butyl]imidazole
1-[2-(4-tert-butylbenzyloxy)-4-(2,4-dichlorophenyl)butyl]imidazole
1-[2-cinnamyloxy-4-(2,4-dichlorophenyl)butyl]imidazole
1-[2-(4-chlorocinnamylthio)-4-(2,4-dichlorophenyl)butyl]imidazole
1-[2-(4-phenylbutylthio)-4-(2,4-dichlorophenyl)butyl]imidazole
1-[2-(4-chlorophenylthio)-4-(4-tert-butylphenyl)butyl]imidazole
1-[2-(2,4-dichlorobenzyloxy)-4-(4-tert-butylphenyl)butyl]imidazole 1-[2-(3,4-dichlorophenylthio)-4-(4-fluorophenyl)-butyl]imidazole
1-[2-(2,4-dichlorobenzyloxy)-4-(4-fluorophenyl)-butyl]imidazole
1-[2-(3,4-dichlorobenzylthio)-4-(4-fluorophenyl)-butyl]imidazole
1-[2-(3,4-dichlorobenzylthio)-4-(2,4-dimethylphenyl)butyl]imidazole
1-[2-(4-chlorophenoxy)-4-(2,4-dimethylphenyl)-butyl]imidazole
trans-1[2-(3,4-dichlorophenylthio)-4-phenylbut-3-enyl]imidazole - oxalate salt, m.p. 171.5°–175.5° C. (dec.).
trans-1-[2-(3,4-dichlorobenzylthio)-4-phenylbut-3-enyl]imidazole — nitrate salt, m.p. 138°–139° C. (foaming)
trans-1-[2-(2,4-dichlorobenzyloxy)-4-phenylbut-3-enyl]imidazole — nitrate salt, m.p. 133.5°–134.5° C. (foaming)
1-[2-(4-chlorobenzylthio)-4-phenylbut-3-enyl]-imidazole
1-[2-(4-chlorophenylthio)-4-phenylbut-3-enyl]-imidazole
1-[2-(4-chlorophenoxy)-4-phenylbut-3-enyl]-imidazole
1-[2-(4-bromobenzylthio)-4-phenylbut-3-enyl]-imidazole
1-[2-(4-fluorophenoxy)-4-phenylbut-3-enyl]imidazole
1-[2-(3-phenylpropyloxy)-4-phenylbut-3-enyl]-imidazole
1-[2-cinnamyloxy-4-phenylbut-3-enyl]imidazole
1-[2-(4-chlorocinnamyloxy)-4-phenylbut-3-enyl]-imidazole
1[2-(4-phenylbutylthio)-4-phenylbut-3-enyl]-imidazole
1-[2-(3,4-dichlorophenylthio)-4-(4-chlorophenyl)but-3-enyl]imidazole
1-[2-(4-chlorophenoxy)-4-(4-chlorophenyl)but-3-enyl]imidazole
1-[2-(2,4,5-trichlorophenylthio)-4-(4-chlorophenyl)-but-3-enyl]imidazole
1-[2-(2,3,4,5,6-pentachlorophenylthio)-4-(4-chlorophenyl)but-3-enyl]imidazole
1-[2-(cinnamylthio)-4-(4-chlorophenyl(but-3-enyl]-imidazole
1-[2-(4-chlorocinnamyloxy)-4-(4-chlorophenyl)but-3-enyl]imidazole
1-[2-(4-chlorophenylthio)-4-(4-chlorophenyl)but-3-enyl]imidazole
1-[2-(4-chlorobenzyloxy)-4-chlorophenyl)but-3-enyl]imidazole
1-[2-(4-chlorobenzylthio)-4-(4-chlorophenyl)but-3-enyl]imidazole
1-[2-(2,4-dichlorobenzyloxy)-4-(4-chlorophenyl)but-3-enyl]imidazole
1-[2-(2,4-dichlorophenylthio)-4-phenylbutyl]-imidazole
1-[2-(4-chlorobenzylthio)-4-phenylbutyl]imidazole
1-[2-(4-chlorobenzyloxy-4-phenylbutyl]imidazole
1-[2-(4-chlorobenzylthio)-4-(4-fluorophenyl)butyl]-imidazole
1-[2-(2,4-dichlorobenzylthio)-4-(4-fluorophenyl)-butyl]imidazole
1-[2-(2,4-dichlorophenylthio)-4-(4-fluorophenyl)-butyl]imidazole — nitrate salt, m.p. 92°–93.5° C
1-[2-(2,6-dichlorophenylthio)-4-(4-chlorophenyl)-butyl]imidazole — nitrate salt, m.p. 162,5°–164.5° C
1-[2-(2,5-dichlorophenylthio)-4-(4-chlorophenyl)-butyl]imidazole — nitrate salt, m.p. 155.5°–157° C.
1-[2-(2,3-dichlorophenylthio)-4-(4-chlorophenyl)-butyl]imidazole
1-[2-(2-chlorophenylthio)-4-(4-chlorophenyl)butyl]-imidazole — nitrate salt, m.p. 134.5°–135.5° C.
1-[2-(3-chlorophenylthio)-4-(4-chlorophenyl)butyl]-imidazole
1-[2-(2-bromophenylthio)-4-(4-chlorophenyl)butyl]-imidazole
1-[2-(4-bromophenylthio)-4-(4-chlorophenyl)butyl]-imidazole
1-[2-(2,6-dibromophenylthio)-4-(4-chlorophenyl)-butyl]imidazole
1-[2-(2,4-dibromophenylthio)-4-(4-chlorophenyl)-butyl]imidazole
1-[2-(2,4,6-trichlorophenylthio)-4-(4-chlorophenyl)-butyl]imidazole
1-[2-(2,6-dichlorophenylthio)-4-(4-fluorophenyl)-butyl]imidazole — nitrate salt, m.p. 131.5°–132.5° C.
1-[2-(2,5-dichlorophenylthio)-4-(4-fluorophenyl)-butyl]imidazole
1-[2-(2,3-dichlorophenylthio)-4-(4-fluorophenyl)-butyl]imidazole
1-[2-(2-chlorophenylthio)-4-(4-fluorophenyl)butyl]-imidazole
1-[2-(4-chlorophenylthio)-4-(4-fluorophenyl)butyl]-imidazole
1-[2-(2-bromophenylthio)-4-(4-fluorophenyl)butyl]-imidazole
1-[2-(4-bromophenylthio)-4-(4-fluorophenyl)butyl]-imidazole
1-[2(2,6-dibromophenylthio)-4-(4-fluorophenyl)-butyl]imidazole
1-[2-(2,4-dibromophenylthio)-4-(4-fluorophenyl)-butyl]imidazole
1-[2-(2,4,5-trichlorophenylthio)-4-(4-fluorophenyl)-butyl]imidazole
1-[2-(2,4,6-trichlorophenylthio)-4-(4-fluorophenyl)-butyl]imidazole — nitrate salt, m.p. 163°–164° C.
1-[2-(2,6-dichlorophenylthio)-4-(4-bromophenyl)-butyl]imidazole
1-[2-(2,5-dichlorophenylthio)-4-(4-bromophenyl)-butyl]imidazole
1-[2-(2,4-dichlorophenylthio)-4-(4-bromophenyl)-butyl]imidazole
1-[2-(2,3-dichlorophenylthio)-4-(4-bromophenyl)-butyl]imidazole
1-[2-(3,4-dichlorophenylthio)-4-(4-bromophenyl)-butyl]imidazole
1-[2-(2-chlorophenylthio)-4-(4-bromophenyl)butyl]-imidazole
1-[2-(3-chlorophenylthio)-4-(4-bromophenyl)butyl]-imidazole
1-[2-(4-chlorophenylthio)-4-(4-bromophenyl)butyl]-imidazole
1-[2-(2-bromophenylthio)-4-(4-bromophenyl)butyl]-imidazole
1-[2-(4-bromophenylthio)-4-(4-bromophenyl)butyl]-imidazole
1-[2-(2,6-dibromophenylthio)-4-(4-bromophenyl)-butyl]imidazole
1-[2-(2,4-dibromophenylthio)-4-(4-bromophenyl)-butyl]imidazole
1-[2-(2,4,5-trichlorophenylthio)-4-(4-bromophenyl)-butyl]imidazole 1-[2-(2,4,6-trichlorophenylthio)-4-(4-bromophenyl)butyl]imidazole
1-[2-(2,6-dichlorophenylthio)-4-(4-trifluoromethylphenyl)butyl]imidazole
1-[2-(2-chlorophenylthio)-4-(4-trifluoromethylphenyl)butyl]imidazole
1-[2-(2,5-dichlorophenylthio)-4-(4-trifluoromethylphenyl)butyl]imidazole
1-[2-(2,4-dichlorophenylthio)-4-(4-trifluoromethylphenyl)butyl]imidazole
1-[2-(2,6-dichlorobenzyloxy)-4-(4-chlorophenyl)butyl]imidazole
1-[2-(2,6-dichlorobenzylthio)-4-(4-chlorophenyl)butyl]imidazole
1-[2-(2-chlorobenzyloxy)-4-(4-chlorophenyl)butyl]imidazole
1-[2-(2-chlorobenzylthio)-4-(4-chlorophenyl)butyl]imidazole
1-[2-(2,3,6-trichlorophenoxy)-4-(4-chlorophenyl)butyl]imidazole
1-[2-(2,4,6-trichlorophenoxy)-4-(4-chlorophenyl)butyl]imidazole — nitrate salt, m.p. 173.5°–174.5° C.
1-[2-(2,5-dichlorophenoxy)-4-(4-chlorophenyl)butyl]imidazole
1-[2-(2,4-dichlorophenoxy)-4-(4-chlorophenyl)butyl]imidazole — nitrate salt, m.p. 130°–131.5° C.
1-[2-(2,6-dichlorophenoxy)-4-(4-chlorophenyl)butyl]imidazole — nitrate salt, m.p. 145.5°–148° C.
1-[2-(2-chlorophenylthio)-5-(4-chlorophenyl)butyl]imidazole
1-[2-(2,6-dichlorophenylthio)-5-(4-chlorophenyl)butyl]imidazole
1-[2-(2,5-dichlorophenylthio)-5-(4-chlorophenyl)pentyl]imidazole
1-[2-(2,4-dichlorophenylthio)-5-(4-chlorophenyl)pentyl]imidazole
1-[2-(2-bromophenylthio)-5-(4-chlorophenyl)pentyl]imidazole
1-[2-(2,6-dichlorophenylthio)-4-(4-chlorophenyl)but-3-enyl]imidazole
1-[2-(2,5-dichlorophenylthio)-4-(4-chlorophenyl)but-3-enyl[imidazole
1-[2-(2-chlorophenylyhio)-4-(4-chlorophenyl)but-3-enyl]imidazole
1-[2-(2-bromophenylthio)-4(4-chlorophenyl)but-3-enyl]imidazole
1-[2-(2,6-dichlorophenoxy)-4-(4-chlorophenyl)but-3-enyl]imidazole
1-[2-(2,4-dichlorophenylthio)-4-(4-chlorophenyl)but-3-enyl]imidazole — nitrate salt, m.p. 149°–150.5° C (foams)
1-[2-(2,4,6-trichlorophenoxy)-4-(4-chlorophenyl)but-3-enyl]imidazole — nitrate salt, m.p. 156°–157° C (foams)
1-[2-(2-chlorophenylthio)-4-(2,4-dichlorophenyl)butyl]imidazole — nitrate salt, m.p. 112°–112.5° C.
1-[2-(4-chlorophenylthio)-4-(2,4-dichlorophenyl)butyl]imidazole — nitrate salt, m.p. 124°–125.5° C. (foams)
1-[2-(2,4-dichlorophenylthio)-4-(2,4-dichlorophenyl)butyl]imidazole — nitrate salt, m.p. 130°–131.5° C.
1-[2-(2-chlorophenoxy)-4-(2,4-dichlorophenyl)butyl]imidazole — nitrate salt, m.p. 116.5–117.5° C.

EXAMPLE 7

Following the procedures in Preparations 3 or 4, and Examples 1; 2,3; or 2,4, using equivalent amounts of the appropriate starting materials, there may be obtained the following compounds. Where indicated, the compounds may be further characterized by conversion to the indicated acid addition salt.

1-[3-(4-chlorophenylthio)-3-(4-chlorophenyl)propyl]imidazole — oxalate salt, m.p. 108°–112° C.
1-[3-(4-chlorobenzylthio)-3-(4-chlorophenyl)propyl]imidazole — oxalate salt, m.p. 115°–156° C.
1-[3-(4-chlorobenzyloxy)-3-(4-chlorophenyl)propyl]imidazole — oxalate salt, m.p. 105°–106° C.
1-[3-(4-bromo-3-methylphenylthio)-3-(4-chlorophenyl)propyl]imidazole — nitrate salt, m.p. 107°–108° C. (dec.)
1-[3-(4-tert-butylphenylthio)-3-(4-chlorophenyl)propyl]imidazole — oxalate salt, m.p. 127.5°–129° C. (dec.)
1-[3-(4-fluorophenylthio)-3-(4-chlorophenyl)propyl]imidazole
1-[3-(4-bromobenzyloxy)-3-(4-chlorophenyl)propyl]imidazole
1-[3-(2,4-dichlorophenylthio)-3-(4-chlorophenyl)propyl]imidazole
1-[3-(3,4-dichlorophenylthio)-3-(4-chlorophenyl)propyl]imidazole
1-[3-(4-trifluoromethylphenylthio)-3-(4-chlorophenyl)propyl]imidazole
1-[3-(4-trifluoromethylbenzyloxy)-3-(4-chlorophenyl)propyl]imidazole
1-[3-(4-chlorocinnamyloxy)-3-(4-chlorophenyl)propyl]imidazole
1-[3-(2,4-dichlorocinnamylthio)-3-(4-chlorophenyl)propyl]imidazole
1-[3-(4-phenylbutyloxy)-3-(4-chlorophenyl)propyl]imidazole
1-[3-(4-methylbenzylthio)-3-(2,4-dichlorophenyl)propyl]imidazole — nitrate salt, m.p. 69.5°–75° C. (dec.)
1-[3-(4-chlorobenzylthio-3-(2,4-dichlorophenyl)propyl]imidazole — nitrate salt, m.p. 63°–66.5° C. (dec.)
1-[3-(4-chlorophenylthio)-3-(2,4-dichlorophenyl)propyl]imidazole — nitrate salt, m.p. 123.5°–125.5° C. (dec.)
1-[3-(2,4-dichlorophenylthio)-3-(2,4-dichlorophenyl)propyl]imidazole
1-[3-(3,4-dichlorophenylthio)-3-(2,4-dichlorophenyl)propyl]imidazole
1-[3-(4-trifluoromethylphenylthio)-3-(2,4-dichlorophenyl)propyl]imidazole
1-[3-(4-trifluoromethylbenzyloxy)-3-(2,4-dichlorophenyl)propyl]imidazole
1-[3-(4-tert-butylphenylthio)-3-(2,4-dichlorophenyl)propyl]imidazole
1-[3-(4-methylbenzyloxy)-3-(2,4-dichlorophenyl)propyl]imidazole
1-[3-(4-chlorocinnamyloxy)-3-(2,4-dichlorophenyl)propyl]imidazole
1-[3-(3,4-dichlorobenzyloxy)-3-(2,4-dichlorophenyl)propyl]imidazole
1-[3-(2,4,5-trichlorophenylthio)-3-(2,4-dichlorophenyl)propyl]imidazole
1-[3-(4-phenylbutylthio)-3-(2,4-dichlorophenyl)propyl]imidazole
1-[3-(4-chlorobenzyloxy)-3-(2,4-dichlorophenyl)propyl]imidazole
1-[3-(2,4-dichlorobenzyloxy)-3-(2,4-dichlorophenyl)propyl]imidazole 1-[3-(4-chlorophenylthio)-3-(4-tert-butylphenyl)-propyl]imidazole
1-[3-(2,4-dichlorobenzylthio)-3-(4-tert-butylphenyl)-propyl]imidazole
1-[3-(2,4,5-trichlorophenylthio)-3-(4-fluorophenyl)-propyl]imidazole — oxalate salt, coalesces 76° C. final m.p. 99° C.
1-[3-(4-chlorobenzylthio)-3-(4-fluorophenyl)propyl]-imidazole
1-[3-(4-tert-butylphenylthio)-3-(4-fluorophenyl)-propyl]imidazole
1-[3-(4-chlorocinnamyloxy)-3-(4-fluorophenyl)-propyl]imidazole
1-[3-(4-chlorocinnamyloxy)-3-(2,4-dimethylphenyl)-propyl]imidazole
1-[3-(2,4-dichlorobenzylthio)-3-(2,4-dimethylphenyl)propyl]imidazole
1-[3-(4-bromophenylthio)-3-(2,4-dimethylphenyl)-propyl]imidazole
1-[3-(4-methylbenzylthio)-3-(4-tert-butylphenyl)-propyl]imidazole — nitrate salt, m.p. 132°-134° C. (dec.)
1-[3-cinnamyloxy-3-(4-tert-butylphenyl)propyl]-imidazole
1-[3-(4-chlorophenylthio)-4-phenylbutyl]imidazole
1-[3-(2,4-dichlorobenzylthio)-4-phenylbutyl]-imidazole
1-[3-(4-tert-butylphenylthio)-4-phenylbutyl]-imidazole
1-[3-(4-chlorocinnamyloxy)-4-phenylbutyl]imidazole
1-[3-(2,4-dichlorophenylthio)-4-(4-chlorophenyl)-butyl]imidazole
1-[3-(4-methylbenzylthio)-4-(4-chlorophenyl)butyl]-imidazole
1-[3-(4-chlorobenzylthio)-4-(4-methylphenyl)butyl]-imidazole
1-[3-(2,4-dichlorophenoxy)-4-(4-methylphenyl)-butyl]imidazole
1-[3-(4-chlorocinnamyloxy)-4-(4-methylphenyl)-butyl]imidazole
1-[3-(2,4-dichlorobenzylthio)-5-(4-chlorophenyl)pentyl]imidazole
1-[3-(4-bromobenzyloxy)-5-(4-chlorophenyl)pentyl]-imidazole
1-[3-(4-chlorobenzylthio)-5-(4-chlorophenyl)pentyl]-imidazole
1-[3-(2,4,5-trichlorophenylthio)-5-(4-chlorophenyl)-pentyl]imidazole
1-[3-(4-tert-butylbenzylthio)-5-(4-chlorophenyl)pentyl]imidazole
1-[3-(3,4-dichlorophenylthio)-3-(2-trifluoromethylphenyl)propyl]imidazole
1-[3-(3,4-dichlorobenzylthio)-3-(2-trifluoromethylphenyl)propyl]imidazole
1-[3-(4-chlorophenylthio)-3-(2,4-dibromophenyl)-propyl]imidazole
1-[3-(4-chlorophenylthio)-3-(2,4-difluorophenyl)-propyl]imidazole
1-[3-(4-fluorophenylthio)-3-(2,4-dichlorophenyl)-propyl]imidazole
1-[3-(4-fluorobenzylthio)-3-(2,4-dichlorophenyl)-propyl]imidazole
1-[3-(2-chlorophenylthio)-4-(4-chlorophenyl)butyl]-imidazole
1-[3-(2,6-dichlorophenylthio)-4-(4-chlorophenyl)-butyl]imidazole
1-[3-(2,5-dichlorophenylthio)-4-(4-chlorophenyl)-butyl]imidazole
1-[3-(2,4-dichlorophenylthio)-4-(4-chlorophenyl)-butyl]imidazole
1-[3-(2-bromophenylthio)-4-(4-chlorophenyl)butyl]-imidazole
1-[3-(2,6-dibromophenylthio)-4-(4-chlorophenyl)-butyl]imidazole
1-[3-(2-chlorophenylthio)-5-(4-chlorophenyl)pentyl]-imidazole
1-[3-(2,6-dichlorophenylthio)-5-(4-chlorophenyl)pentyl]imidazole
1-[3-(2,5-dichlorophenylthio)-5-(4-chlorophenyl)pentyl]imidazole
1-[3-(2,4-dichlorophenylthio)-5-(4-chlorophenyl)pentyl]imidazole
1-[3-(2-bromophenylthio)-5-(4-chlorophenyl)pentyl]-imidazole

EXAMPLE 8

Following the procedures in Preparation 4, and Examples 1; 2,3; or 2,4, using equivalent amounts of the appropriate starting materials, there may be obtained the following compounds. Where indicated, the compounds may be further characterized by conversion to the indicated acid addition salt.

1-[4-(3,4-dichlorophenylthio)-4-(4-(4-chlorophenyl)-butyl]imidazole — nitrate salt, m.p. 100°-104.5° C., oxalate salt m.p. 118°-123° C. (foaming)
1-[4-(3,4-dichlorophenoxy)-4-(4-chlorophenyl)butyl]-imidazole — nitrate salt, m.p. 128°-130.5° C.
1-[4-(4-chlorobenzylthio)-4-(4-chlorophenyl)butyl]-imidazole — nitrate salt, m.p. 123°-125° C. (foaming)
1-[4-(2,4-dichlorobenzyloxy)-4-(4-chlorophenyl)-butyl]imidazole — nitrate salt, m.p. 91°-114° C.
1-[4-(3,4-dichlorobenzyloxy-4-(4-chlorophenyl)-butyl]imidazole
1-[4-(4-bromobenzylthio)-4-(4-chlorophenyl)butyl]-imidazole
1-[4-(4-fluorophenylthio)-4-(4-chlorophenyl)butyl]-imidazole
1-[4-(4-methylbenzyloxy)-4-(4-chlorophenyl)butyl]-imidazole
1-[4-(4-chlorophenylthio)-4-(2,4-dichlorophenyl)-butyl]imidazole — oxalate salt, m.p. 69°-75° C. (foaming)
1-[4-(4-methylphenylthio)-4-(2,4-dichlorophenyl)-butyl]imidazole
1-[4-(4-chlorobenzylthio)-4-(2,4-dichlorophenyl)-butyl]imidazole — oxalate salt, m.p. 62.5°-65° C. (foaming)
1-[4-benzylthio-4-(2,4-dichlorophenyl)butyl]-imidazole
1-[4-(2,4-dichlorobenzyloxy)-4-(2,4-dichlorophenyl)-butyl]imidazole
1-[4-(4-chlorobenzyloxy)-4-(2,4-dichlorophenyl)-butyl]imidazole — nitrate salt, coalesces 98.5° C., final m.p. 108° C.
1-[4-(4-phenylbutylthio)-4-(2,4-dichlorophenyl)-butyl]imidazole
1-[4-(4-fluorobenzylthio)-4-(2,4-dichlorophenyl)-butyl]imidazole — oxalate salt, m.p. 95°-101.5° C.
1-[4-(4-tert-butylphenylthio)-4-(4-fluorophenyl)-butyl]imidazole
1-[4-(3,4-dichlorophenylthio)-4-(4-fluorophenyl)-butyl]imidazole
1-[4-(4-tert-butylbenzyloxy)-4-(4-fluorophenyl)-butyl]imidazole — oxalate salt, m.p. 49.5°-51° C.

1-[4-phenylpropylthio-4-(4-fluorophenyl)butyl]-
imidazole — oxalate salt, m.p. 97°–99° C.
1-[4-phenylthio-4-(4-tert-butylphenyl)butyl]-
imidazole nitrate salt, m.p. 121.5°–123.5° C. (dec.)
1-[4-(4-chlorophenylthio)-4-(4-tert-butylphenyl)-
butyl]imidazole
1-[4-(2,4-dichlorobenzylthio)-4-(4-tert-butylphenyl)-
butyl]imidazole
1-[4-(4-fluorophenylthio)-4-(2,4-dimethylphenyl)-
butyl]imidazole
1-[4-cinnamyloxy-4-(2,4-dimethylphenyl)butyl]-
imidazole
1-[4-(4-methylbenzylthio)-4-(4-bromophenyl)butyl]-
imidazole — nitrate salt, m.p. 93°–95° C. (dec.)
1-[4-(4-bromobenzyloxy)-4-(4-bromophenyl)butyl]-
imidazole — nitrate salt, m.p. 117°–123.5° C.
1-[4-(4-chlorophenylthio)-5-phenylpentyl]imidazole
1-[4-(2,4-dichlorobenzylthio)-5-phenylpentyl]-
imidazole
1-[4-(4-tert-butylphenoxy)-5-phenylpentyl]imidazole
1-[4-(4-chlorocinnamyloxy)-5-phenylpentyl]-
imidazole
1-[4-(2,4-dichlorophenylthio)-5-(4-chlorophenyl)pen-
tyl]imidazole
1-[4-(4-methylbenzylthio)-5-(4-chlorophenyl)pentyl]-
imidazole
1-[4-(2,4-dichlorobenzylthio)-6-(4-chlorophenyl)hex-
yl]imidazole
1-[4-(4-bromobenzyloxy)-6-(4-chlorophenyl)hexyl]-
imidazole
1-[4-(4-chlorobenzylthio)-6-(4-chlorophenyl)hexyl]-
imidazole
1-[4-(2,4,5-trichlorophenylthio-6-(4-chlorophenyl)-
hexyl]imidazole
1-[4-(4-tert-butylbenzylthio)-6-(4-chlorophenyl)hex-
yl]imidazole
1-[4-(4-trifluoromethylphenylthio)-6-(4-chloro-
phenyl)hexyl]imidazole
1-[4-(4-trifluoromethylbenzyloxy)-6-(4-chloro-
phenyl)hexyl]imidazole
1-[6-(2,4-dichlorobenzyloxy)-6-phenylhexyl]-
imidazole
1-[6-(4-chlorobenzylthio)-6-phenylhexyl]imidazole
1-[6-(4-methylphenylthio)-6-phenylhexyl]imidazole
1-[6-(4-chlorophenylthio)-6-phenylhexyl]imidazole
1-[6-(4-chlorobenzyloxy)-6-(4-chlorophenyl)hexyl]-
imidazole
1-[6-benzylthio-6-(4-chlorophenyl)hexyl]imidazole
1-[6-(4-fluorobenzylthio)-6-(4-chlorophenyl)hexyl]-
imidazole
1-[6-(3,4-dichlorobenzyloxy)-6-(4-chlorophenyl)hex-
yl]imidazole
1-[6-cinnamyloxy-6-(4-chlorophenyl)hexyl]imidazole
1-[6-(2,4-dichlorobenzyloxy)-7-(4-chlorophenyl)hep-
tyl]imidazole
1-[6-(2,4-dichlorobenzylthio)-8-phenyloctyl]-
imidazole
1-[6-(4-chlorobenzyloxy)-10-phenyldecyl]imidazole
1-(9-benzyloxy-9-phenylnonyl)imidazole
1-[9-(4-fluorophenylthio)-9-phenylnonyl]imidazole
1-[9-phenoxy-9-(4-chorophenyl)nonyl]imidazole
1-[9-(2,4,5-trichlorobenzylthio)-9-(4-chloropheny)
nonyl]imidazole
1-[9-cinnamyloxy-9-(4-chlorophenyl)nonyl]imidazole
1-[9-(2,4-dichlorobenzyloxy)-10-(4-chorophenyl)-
decyl]imidazole
1-[9-(2,4-dichlorobenzylthio)-11-phenylundecyl]-
imidazole
1-[9-(4-chlorobenzyloxy)-13-phenyltridecyl]-
imidazole
1-[4-(4-fluorophenylthio)-4-(2,4-dichlorophenyl)-
butyl]imidazole.

EXAMPLE 9

Nitric acid (70%; d = 1.42) was added dropwise to a stirred solution of 2.0 g. of 1-[2-(2,4-dichlorobenzyloxy)-4-phenylbutyl]imidazole in 30 ml. of anhydrous ether until precipitation was complete. The product was filtered off, washed with ether, air dried, and recrystallized from ethyl acetate to yield 1-[2-(2,4-dichlorobenzyloxy)-4-phenylbutyl]imidazole nitrate, m.p. 121°—124° C.

In similar manner, all compounds of Formula (I) in base form can be converted to their antimicrobial acid addition salts by treatment with the appropriate acid, for example, hydrochloric acid, hydrobromic acid, sulfuric acid, nitric acid, phosphoric acid, acetic acid, propionic acid, glycolic acid, lactic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid or salicyclic acid.

EXAMPLE 10

1-[2-(2,4-Dichlorobenzyloxy)-4-phenylbutyl]-imidazole nitrate (2.0 g.) in 100 ml. of dichloromethane was shaken with excess dilute potassium carbonate solution until the salt was completely dissolved. The organic layer was then separated, washed twice with water, dried over magnesium sulfate and evaporated to yield 1-[2-(2,4-dichlorobenzyloxy-4-phenylbutyl]-imidazole as an oil.

In similar manner, the antimicrobial acid addition salts of all compounds of Formula (I) can be converted to the corresponding compounds in base form.

EXAMPLE 11

The following illustrates the preparation of representative pharmaceutical formulations which may be used for controlling fungi, bacteria and protozoa, utilizing an active compound such as salt of 1-[2-(3,4-dichlorophenylthio)-4-phenylbutyl]imidazole.

| A. | Topical Formulation | | grams |
|---|---|---|---|
| | Active compound | | 0.2 – 2 |
| | Span 60 | | 2 |
| | Tween 60 | | 2 |
| | Mineral oil | | 5 |
| | Petrolatum | | 10 |
| | Methyl paraben | | 0.15 |
| | Propyl paraben | | 0.05 |
| | BHA (butylated hydroxy anisole) | | 0.01 |
| | Water | qs | 100 |

All of the above ingredients, except water, are combined and heated at 60° C. with stirring. A sufficient quantity of water at 60° C. in then added with vigorous stirring to provide 100 g. of the cream formulation which is then cooled to room temperature.

| B | I.V. Formulation | |
|---|---|---|
| | Active compound | 0.5 g. |
| | Propylene glycol | 20 g. |
| | Polyethylene glycol 400 | 20 g. |
| | Tween 80 | 1 g. |

| B | I.V. Formulation | |
|---|---|---|
| | 0.9 Saline solution qs | 100 ml. |

The active compound is dissolved in propylene glycol, polyethylene glycol 400 and Tween 80. A sufficient quantity of 0.9% saline solution is then added with stirring to provide 100 ml. of the I.V. solution which is filtered through a 0.2 micron membrane filter and packaged under sterile conditions.

| C. | Oral Formulation | parts by weight |
|---|---|---|
| | Active compound | 200 |
| | Magnesium stearate | 3 |
| | Starch | 30 |
| | Lactose | 116 |
| | PVP (polyvinylpyrrolidone) | 3 |

The above ingredients are combined and granulated using methanol as the solvent. The formulation is then dried and formed into tablets (containing 200 mg. of active compound) with an appropriate tabletting machine.

I claim as my invention:

1. A compound of the formula

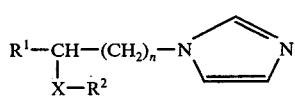  (I)

wherein $R^1$ is phenethyl, phenylpropyl or styryl and $R^2$ is phenyl, phenyl straight chain lower alkyl or phenyl straight chain alkenyl, wherein the phenyl rings of $R^1$ and $R^2$ may independently be unsubstituted or substituted with one or more substituents independently selected from the group consisting of lower akyl of from one to four carbon atoms, halo and trifluoromethyl; X is oxygen or sulfur; $n$ is an integer of from one to three; and the antimicrobial acid addition salts therof.

2. The compound of claim 1 wherein $n$ is 1.

3. The compound of claim 1 wherein $R^1$ is halo-substituted phenethyl or styryl.

4. The compound of claim 3 wherein $R^1$ has a 4-halo substituent.

5. The compound of claim 3 wherein, when $R^1$ has more than one halo substituent, all such substituents are the same halo.

6. The compound of claim 3 wherein the halo substituent on $R^1$ is chloro.

7. The compound of claim 3 wherein $R^2$ is substituted or unsubstituted phenyl or benzyl.

8. The compound of claim 7 wherein $R^2$ is halo-substituted phenyl or benzyl.

9. The compound of claim 8 wherein $R^2$ is phenyl having at least one ortho-halo substituent.

10. The compound of claim 9 wherein, when $R^2$ has more than one halo substituent, all such substituents are the same halo.

11. The compound of claim 8 wherein the halo substituent on $R^2$ is chloro.

12. The compound of claim 9 wherein X is sulfur.

13. The compound of claim 8 wherein $R^2$ is halo-substituted benzyl.

14. The compound of claim 13 wherein $R^2$ is chloro-substituted benzyl.

15. The compound of claim 8 which is 1-[2-(2,6-dichlorophenylthio)-4-(4-chlorophenyl)butyl]imidazole and the antimicrobial acid addition salts thereof.

16. The compound of claim 8 which is 1-[2-(2,5-dichlorophenylthio)-4-(4-chlorophenyl)butyl]imidazole and the antimicrobial acid addition salts thereof.

17. The compound of claim 8 which is 1-[2-(2,4-dichlorophenylthio)-4-(4-chlorophenyl)butyl]imidazole and the antimicrobial acid addition salts thereof.

18. The compound of claim 8 which is 1-[2-(2-chorophenylthio)-4-(4-chlorophenyl)butyl]imidazole and the antimicrobial acid addition salts thereof.

19. The compound of claim 8 which is 1-[2-(2,3-dichlorophenylthio)-4-(4-chorophenyl)butyl]imidazole and the antimicrobial acid addition salts thereof.

20. The compound of claim 8 which is 1-[2-(2-bromophenylthio)-4-(4-chlorophenyl)butyl]imidazole and the antimicrobial acid addition salts thereof.

21. The compound of claim 8 which is 1-[2-(2,6-dibromophenylthio)-4-(4-chorophenyl)butyl]imidazole and the antimicrobial acid addition salts thereof.

22. The compound of claim 8 which is 1-[2-(2,4,6-trichlorophenylthio)-4-(4-fluorophenyl)butyl] imidazole and the antimicrobial acid addition salts thereof.

23. The compound of claim 8 which is 1-[2-(2,6-dichlorophenylthio)-4-(4-fluorophenyl)butyl] imidazole and the antimicrobial acid addition salts thereof.

24. The compound of claim 8 which is 1-[2-(2,6-dichlorophenylthio)-4-(4-chlorophenyl)but-3-enyl]-imidazole and the antimicrobial acid addition salts thereof.

25. The compound of claim 8 which is 1-[3-(2,6-dichlorophenylthio)-5-(4-chlorophenyl)pentyl]-imidazole and the antimicrobial acid addition salts thereof.

26. The compound of claim 8 which is 1-[2-(2,5-dichlorophenylthio)-4-(4-fluorophenyl)butyl]imidazole and the antimicrobial acid addition salts thereof.

27. The compound of claim 8 which is 1-[2-(2,4,5-trichlorophenylthio)-4-(4-fluorophenyl)butyl]imidazole and the antimicrobial acid addition salts thereof.

28. The compound of claim 8 which is 1-[2-(2,4,5-trichlorophenylthio)-4-(4-chlorophenyl)butyl]imidazole and the antimicrobial acid addition salts thereof.

29. A composition useful for inhibiting the growth of fungi, bacteria or portozoa which comprises an effective amount of a compound of the formula

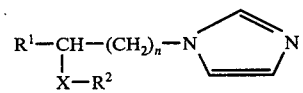  (I)

wherein $R^1$ is phenethyl, phenylpropyl or styryl and $R^2$ is phenyl, phenyl straight chain lower alkyl or phenyl straight chain lower alkenyl, wherein the phenyl rings of $R^1$ and $R^2$ may independently be unsubstituted or substituted with one or more substituents independently selected from the group consisting of lower alkyl of from one to four carbon atoms, halo and trifluoromethyl; X is oxygen or sulfur, $n$ is an integer of from 1 to 3; or an anti-microbial acid addition salt thereof; in admixture with a suitable carrier.

30. The composition of claim 29 suitable for pharmaceutical use wherein the carrier is a pharmaceutically acceptable, non-toxic carrier.

31. The composition of claim 30 for topical administration wherein the compound of Formula I is present as between about 0.1 and 10.0 weight percent of the composition.

32. A method of inhibiting the growth of fungi, bacteria or protozoa which comprises applying to a host object containing, or subject to attack by, fungi, bacteria or protozoa an effective amount of a compound of the formula

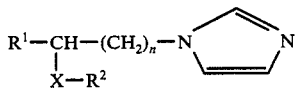

wherein R¹ is phenyl, phenylpropyl or styryl and R² is phenyl, phenyl straight chain lower alkyl or phenyl straight chain lower alkenyl wherein the phenyl rings of R¹ and R² may independently be unsubstituted or substituted with one or more substituents independently selected from the group consisting of lower alkyl of from one to four carbon atoms, halo and trifluoromethyl; X is oxygen or sulfur; $n$ is a integer of from 1 to 3; or an antimicrobial acid addition salt thereof, or a composition containing same as an active ingredient.

33. The method of claim 32 wherein the compound of Formula I is administered topically.

34. The method of claim 32 wherein the compound of Formula I is administered orally or parenterally.

35. The compound 1-[3-(2,6-dichlorophenylthio)-4-(4-chlorophenyl)butyl]imidazole and the antimicrobial acid addition salts thereof.

* * * * *

UNITED STATES PATENT AND TRADEMARK OFFICE

CERTIFICATE EXTENDING PATENT TERM
UNDER 35 U.S.C. 156

Patent No.    : 4,078,071

Dated         : March 7, 1978

Inventor(s)   : Keith A. M. Walker

Patent Owner  : Syntex (U.S.A.) Inc.

This is to certify that there has been presented to the

COMMISSIONER OF PATENTS AND TRADEMARKS an application under 35 U.S.C. 156 for an extension of the patent term. Since it appears that the requirements of law have been met, this certificate extends the term of the patent for the period of

2 YEARS with all rights pertaining thereto as provided by 35 USC 156(b).

I have caused the seal of the Patent and Trademark Office to be affixed this <u>Nineteenth</u> day of <u>December 1986</u>.

Donald J. Quigg

Assistant Secretary and Commissioner of Patents and Trademarks